United States Patent [19]

Ishikawa

[11] 4,095,587

[45] Jun. 20, 1978

[54] HEALTHY MAGNETIC ORNAMENT

[75] Inventor: Mutsuo Ishikawa, Tokyo, Japan

[73] Assignee: TDK Electronics Co., Ltd., Tokyo, Japan

[21] Appl. No.: 679,489

[22] Filed: Apr. 22, 1976

[30] Foreign Application Priority Data

Dec. 22, 1975 Japan .......................... 50-173306[U]

[51] Int. Cl.² .............................................. A61N 1/42
[52] U.S. Cl. ........................................ 128/1.3; 63/4
[58] Field of Search ................. 128/1.3, 1.5, 362, 379; 63/4, 18, DIG. 2, 1 R, 2; 335/296, 302, 306; 252/62.57

[56] References Cited

U.S. PATENT DOCUMENTS

| 1,042,918 | 10/1912 | Houck ................................ 63/4 X |
| 3,677,947 | 7/1972 | Ray et al. ........................ 335/302 X |
| 3,885,383 | 5/1975 | Tanaka ............................... 63/4 X |

FOREIGN PATENT DOCUMENTS

| 259,271 | 10/1963 | Australia .............................. 128/1.3 |
| 995,367 | 8/1951 | France ................................. 128/1.3 |
| 15,987 of | 1884 | United Kingdom ................ 128/1.3 |
| 835,646 | 5/1960 | United Kingdom ................ 128/1.3 |
| 1,413,090 | 11/1975 | United Kingdom ..................... 63/4 |

*Primary Examiner*—William E. Kamm
*Attorney, Agent, or Firm*—Armstrong, Nikaido, Marmelstein & Kubovcik

[57] ABSTRACT

A magnetic ornament, such as a bracelet, a necklace or a chain belt, suitable for promoting good health and personal adornment is provided. The magnetic ornament is comprised of at least one capsule linked with at least one chain. The capsule has enclosed therein one or more pieces of a rare earth- cobalt permanent magnet having the magnetic poles formed on the peripheral surface. At least the surfaces of the capsule and the chain are made of non-magnetic corrosion-resistant metal.

3 Claims, 7 Drawing Figures

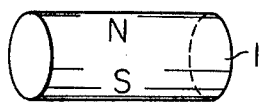
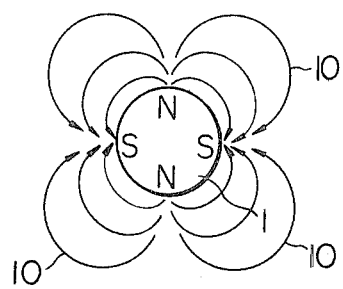
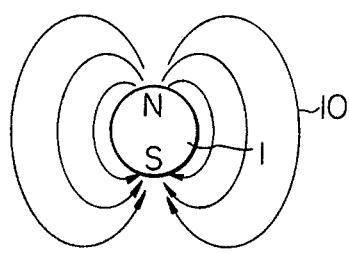
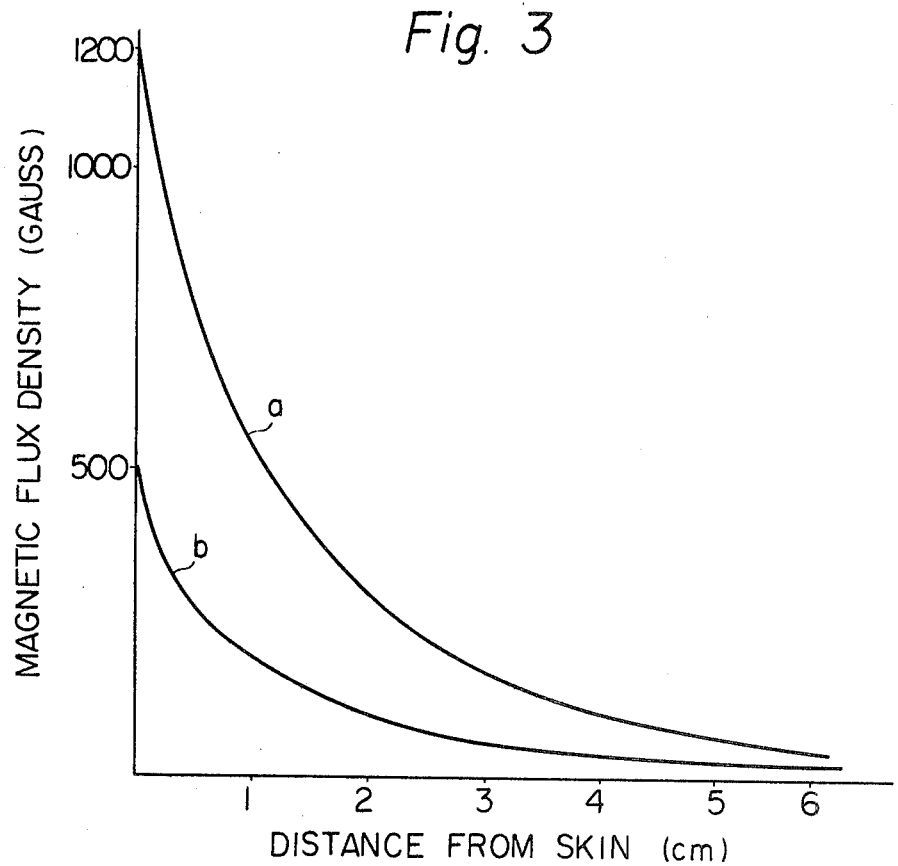

HEALTHY MAGNETIC ORNAMENT

This invention relates to improved magnetic ornaments suitable for healthy, personal adornment. More particularly, it relates to ornaments such as necklace, bracelet and chain belt which are provided with permanent magnets and suitable for both promoting good health and personal adornment.

A variety of healthy, magnetic ornaments have been heretofore proposed. However, these ornaments are not satisfactory in that they have at least one of the following disadvantages. That is, they are poor in good health promotion effect, ornamental effect, or are harmfull to the skin, or they are not enjoyable or pleasing to the wearer. That is, pieces of permanent magnets used in most of the known healthy, magnetic ornaments are made of ferrite. However, ferrite magnets possess small coercive force, residual magnetic flux density and energy product, and therefore, are poor in good health promotion effect. If the size of each piece is made large for the purpose of enhancing the good health promotion effect, the ornaments would not be enjoyable or pleasing to the wearer and would become poor in ornamental effect. Further, some healthy, magnetic ornaments are of a structure such that each piece of permanent magnet is inserted in a case of non-magnetic metal and the case is linked with a non-magnetic metal chain; however, the non-magnetic metal used is sometimes effected by perspiration and is dissolved therein although in a trace amount, and the dissolved metal has a bad effect on the skin of the wearer.

It is an object of the present invention, therefore, to provide a magnetic ornament suitable for promotion of good health and personal adornment which possesses none of the above-mentioned disadvantages.

In accordance with the present invention there is provided a magnetic ornament suitable for both the promotion of good health and personal adornment which comprises at least one capsule linked with at least one chain made of a non-magnetic corrosin-resistant metal, said capsule being made of either a non-magnetic corrosion-resistant metal or a non-magnetic metal plated with a non-magnetic corrosion-resistant metal and said capsule having enclosed therein one or more pieces of a rare earth-cobalt permanent magnet having at least one pair of poles formed on the peripheral surface.

The healthy, magnetic ornament of the invention will be illustrated with reference to the accompanying drawings, in which:

FIGS. 1A and 1B are perspective and side views, respectively, of a piece of a rare earth-cobalt permanent magnet used in the ornament of the invention;

FIG. 2 is a side view of another piece of the rare earth-cobalt permanent magnet;

FIG. 3 is a graph showing the relationship between the magnetic flux density and the distance from the skin;

Figure 4A:
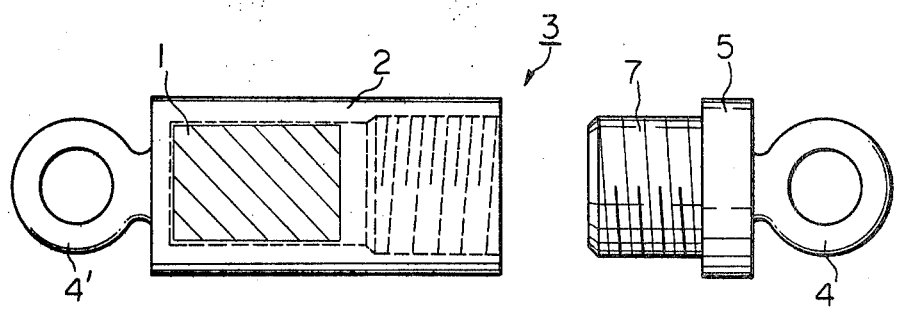
FIGS. 4A and 4B are front and side views, respectively, of a capsule of the ornament of the invention.

In FIGS. 1A and 1B, a cylindrical piece 1 of a rare earth element cobalt magnet (hereinafter referred to as an "RE-Co magnet" for brevity) is magnetized in the direction perpendicular to the axis A of the cylinder, i.e. in the radial direction, so that one or more N-poles and one or more S-poles are formed on two straight lines, respectively, which extend on the peripheral surface in the axial direction with axes B passing through the poles. Lines of magnetic force are formed as shown by reference numeral 10 in FIG. 1B. That is, the magnetic flux density is large in the vicinity of the magnetic poles on the peripheral surface. Therefore, when the RE-Co magnet 1 is used in a manner such that the peripheral surface, particularly the magnetic poles, is adjacent to the skin, the magnetic force exerts a more favorable influence upon the human body than known magnets magnetized in the axial direction.

FIG. 2 shows another RE-Co magnet piece in the form of a cylinder which possesses two pairs of N-poles and S-poles on the periphery of the cross section cut perpendicularly to the axis. The pairs of the N-poles and S-poles are formed on four straight lines, respectively, which extend on the peripheral surface in the axial direction. This magnet has a magnetic flux density larger than that of the magnet shown in FIG. 1B. Thus, an RE-Co magnet having a plurality of pairs of N-poles and S-poles on the periphery is preferred.

FIG. 3 shows the relationship of the magnetic flux density as measured on the skin to the distance from the skin of the periphery of the magnet. Curves a and b indicate a samarium cobalt permanent magnet (as one example of the RE-Co permanent magnets) and a ferrite permanent magnet, respectively. Although the magnetic flux density decreases as the distance from the skin to the magnet increases, the samarium cobalt permanent magnet exhibits a very large magnetic flux density and magnetic field gradient, particularly when said distance is very small.

Figure 4B:
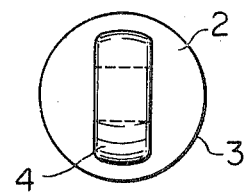

FIGS. 4A and 4B are front and side views, respectively, of the disassembled capsule 3. The capsule 3 is comprised of a cylindrical case 2 with a link 4' and a cap 5 with a link 4. A cylindrical RE-Co magnet rod 1 magnetized in the radial direction is inserted in the cylindrical case 2, so that the magnet rod 1 and the case 2 are coaxial, and the screw part 7 of the cap 5 is screwed into the case 2. The cylindrical case 2 and the cap 5 are made of a non-magnetic corrosion-resistant metal such as gold, platinum or rhodium so that they are not affected by perspiration. Alternatively the case 2 and the cap 5 may be made of a non-magnetic but corrosive metal such as brass, provided that they are thereafter plated with a non-magnetic corrosion-resistant metal.

The capsule 3 may be of any decorative design and of a shape other than the cylindrical shape. However, the cylindrical shape is most preferable because it is enjoyable and pleasing to the wearer.

Figure 5:
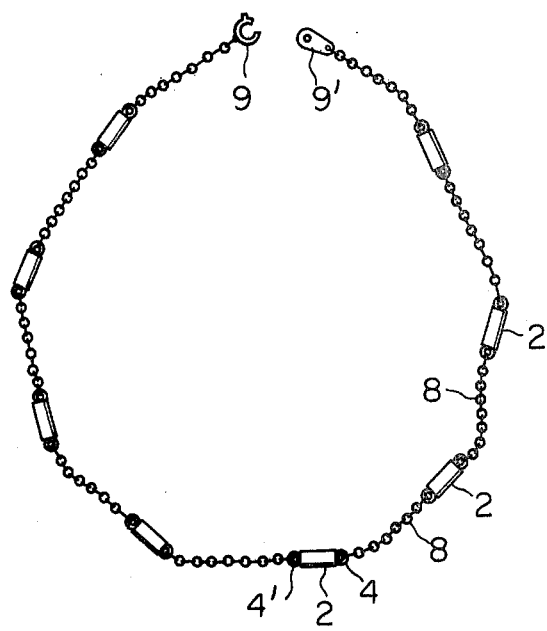
FIG. 5 is a necklace of the invention.

FIG. 5 shows a necklace comprised of a plurality of capsules 2 shown in FIG. 4 and a plurality of chains 8. The chains 8 are made of a non-magnetic corrosion-resistant metal. The necklace is provided with connections 9 and 9' at its ends.

The healthy, magnetic ornament of the invention may be, instead of the necklace illustrated above, a bracelet, a chain belt or the like.

The permanent magnet material used in the magnetic ornament of the invention is comprised of a rare earth element and cobalt. The permanent magnet material includes, for example, $Sm\text{-}Co_5$, $Sm_2\text{-}Co_{17}$, $Ce\text{-}Co_5$, $Ce_2\text{-}Co_{17}$, $Pr\text{-}Co_5$, $Pr_2\text{-}Co_{17}$, $Y\text{-}Co_5$, $Y_2\text{-}Co_{17}$, $La\text{-}Co_5$ and $La_2\text{-}CO_{17}$. It includes further a modified RE-Co material which is prepared by replacing a part of the cobalt with another metal such as copper, iron or manganese.

The magnetic ornament of the invention is characterized particularly in that, first, the permanent magnet pieces are made of a rare earth-cobalt permanent magnetic material and, second, said magnet pieces are magnetized in the radial direction and possess magnetic poles on the peripheral surface. An RE-Co permanent magnet exhibits large coercive force, residual magnetic flux density and energy product as compared with other known permanent magnets. For example, a samarium-cobalt permanent magnet $SmCO_5$ exhibits energy product of approximately 26 MG Oe. In contrast, a known magnetically an anisotropic barium-ferrite permanent magnet exhibits an energy product of approximately 4.5. Therefore, the magnetic pieces used in the magnetic ornament of the invention may be smaller in size than those of known magnetic ornaments. Consequently, the magnetic ornament of the invention is more suitable for promotion of good health, that is, it facilitates blood circulation and, hence, has a favorable effect on the removal of stiffness in the shoulders and muscular pain. Further, the outer surfaces of the magnet ornament are made of a corrosion-resistant such as noble metals and, hence, the magnet ornament is not harmful to the skin and exhibits good ornamental effects. ion-resistant such as noble metals and, hence, the magnet ornament is not harmful to the skin and exhibits good ornamental effects.

What we claim is:

1. A magnetic ornament for use in the promotion of good health and for personal adornment, said ornament comprising at least one capsule, having end faces, of a non-magnetic metal having a corrosion resistant surface, said capsule having a first axis through the end faces thereof, said capsule having a hollow interior; at least one chain of a non-magnetic, corrosion-resistant metal, said chain being linked to the end faces of said capsule; and at least one piece of a rare earth cobalt permanent magnet completely enclosed within the hollow interior of said capsule, said permanent magnet having a peripheral surface and two end faces wherein at least one pair of diametrically opposed poles are formed on said peripheral surface, said magnet having a first axis passing through said end faces, parallel to the first axis of said capsule, and a second axis passing through said pair of diametrically opposed poles, wherein said first axis of said magnet is perpendicular to said second axis and lies in the plane of said ornament which said ornament is lying in a flat plane.

2. A magnetic ornament according to claim 1 wherein said rare earth element-cobalt permanent magnet piece is in the form of a cylinder having at least one pair of magnetic poles on the periphery of the circular cross section cut perpendicularly to the cylinder axis.

3. A magnetic ornament according to claim 1 wherein said capsule is comprised of a cylindrical case and a cylindrical cap, a portion of said cap being screwed into said case.

* * * * *